United States Patent
Grodzki et al.

(10) Patent No.: US 11,647,918 B2
(45) Date of Patent: May 16, 2023

(54) METHOD AND DIAGNOSTIC EXAMINATION DEVICE FOR ESTIMATING AN EXAMINATION DURATION THAT IS TOLERABLE BY A PATIENT

(71) Applicant: Siemens Healthcare GmbH, Erlangen (DE)

(72) Inventors: David Grodzki, Erlangen (DE); Hans Weber, Erlangen (DE)

(73) Assignee: Siemens Healtchare GmbH

( * ) Notice: Subject to any disclaimer, the term of this patent is extended or adjusted under 35 U.S.C. 154(b) by 868 days.

(21) Appl. No.: 16/448,806

(22) Filed: Jun. 21, 2019

(65) Prior Publication Data

US 2019/0387999 A1 Dec. 26, 2019

(30) Foreign Application Priority Data

Jun. 22, 2018 (EP) .................................... 18179343

(51) Int. Cl.
*A61B 5/00* (2006.01)
*A61B 5/055* (2006.01)
*G01R 33/56* (2006.01)

(52) U.S. Cl.
CPC ............ *A61B 5/055* (2013.01); *A61B 5/0046* (2013.01); *A61B 5/7207* (2013.01); *G01R 33/56* (2013.01)

(58) Field of Classification Search
CPC .............................. A61B 5/055; A61B 5/7207
See application file for complete search history.

(56) References Cited

U.S. PATENT DOCUMENTS

| | | |
|---|---|---|
| 2004/0064061 A1 | 4/2004 | Nissila |
| 2013/0023781 A1 | 1/2013 | Freeman et al. |
| 2017/0007148 A1* | 1/2017 | Kaditz .................. A61B 5/055 |
| 2017/0119297 A1 | 5/2017 | Flax et al. |
| 2019/0008397 A1 | 1/2019 | Fine et al. |

FOREIGN PATENT DOCUMENTS

| | | |
|---|---|---|
| AU | 2015264875 A1 | 12/2015 |
| CN | 107767928 A | 3/2018 |
| EP | 1402817 A1 | 3/2004 |
| EP | 3438688 A1 | 2/2019 |
| WO | 2016201499 A1 | 12/2016 |
| WO | 2017072568 A1 | 5/2017 |
| WO | 2019052062 A1 | 3/2019 |

OTHER PUBLICATIONS

European Search Report No. 18179343.1-1126, dated Dec. 14, 2018.
European Office Action No. 18179343.1-1126, dated Mar. 14, 2019.

* cited by examiner

*Primary Examiner* — Joseph M Santos Rodriguez
(74) *Attorney, Agent, or Firm* — Banner & Witcoff Ltd.

(57) ABSTRACT

In a method and apparatus for determining an examination duration tolerable by a patient in and/or on a diagnostic examination device, the patient to be examined is observed at least in a preliminary stage of the examination concerned, during which measurement parameters are ascertained. From the measurement parameters, an algorithm determines a statement about the dwell capability of the patient in the examination device. The algorithm can be an artificial neural network.

16 Claims, 2 Drawing Sheets

METHOD AND DIAGNOSTIC EXAMINATION DEVICE FOR ESTIMATING AN EXAMINATION DURATION THAT IS TOLERABLE BY A PATIENT

BACKGROUND OF THE INVENTION

Field of the Invention

The present invention concerns a method for determining an examination duration which a patient can be expected to tolerate in and/or on a diagnostic examination device. Furthermore, the invention concerns a corresponding examination apparatus, and a non-transitory computer-readable data storage medium that implement such a method.

Description of the Prior Art

The quality of examinations on patients in diagnostic examination devices, for example in a magnetic resonance imaging device (MRI device or MRI examination device), and their duration are influenced by various factors. For example, in the case of a comparatively longer dwell capability of the patient in question in the examination device, in particular when using imaging methods, usually comparatively higher resolution images of the body region of the patient to be examined can be obtained.

In this respect, measures such as, for example, increasing the signal-to-noise ratio (SNR) by averaging or the recording of a more dense matrix, usually increase the quality of, for example, magnetic resonance images, and thus also their diagnostic content.

At the same time, however, the duration of recording and thus of examination are also increased, and consequently the period of time which a patient must spend, for example, motionless in the tunnel of an MRI examination device. The same applies, for example, to additional magnetic resonance imaging with further contrasts as in the case of, for example, diffusion in breast imaging.

However, if the patient is incapable of remaining calmly in the examination device in question for the required time, as a rule the image quality is greatly reduced by artifacts, or the examination may even have to be aborted. The ability concerned, which is often influenced by environmental factors currently affecting the patient, is also referred to as the dwell capability of the patient.

Conventionally, examinations of patients in or on examination devices, for example, in MRI devices, frequently have been aborted if the patient no longer has or can muster the necessary dwell capability. If the image quality is too severely impaired by artifacts, usually a new examination is arranged at a later stage. This is associated with additional costs and additional time for reserving the examination device.

For particularly important images, there is also the strategy of first recording a version of the image with a poorer image quality and shorter recording time, followed by obtaining a version of the image with the high image quality that is actually desired, which is associated with a longer recording time.

This backup strategy results in valuable time of the dwell capability being wasted, which could otherwise have been used to record further contrasts, or for higher resolution recording. For example, it is possible for the patient to have a dwell capability that is sufficient for the desired image quality but not also for the previous recording of the image with lower image quality. In this case, applying the backup strategy will result in failure to record with the image quality actually desired although this would have been possible without applying the backup strategy.

It is therefore desirable to be able to make a statement about the current dwell capability of the patient concerned at an early stage in an examination or, better still, before starting the examination.

SUMMARY OF THE INVENTION

An object of the present invention is to provide a method with which the dwell capability to be expected, or, in other words, an examination duration tolerable for the patient, in and/or on an examination device, can be determined or at least estimated with a high degree of reliability.

A tolerable examination duration as used herein means a period of time during which the particular patient can be examined by means of the examination device but after which the examination must either be aborted (for example, because the patient otherwise experiences pain or suffers an injury) or after which the examination can only be continued by sacrificing quality (for example, above a predetermined threshold).

For example, slight movements by a patient toward the end of the patient's dwell capability may still be acceptable, but terminate the examination duration tolerable if the movements of the patient become so strong that (in accordance with a respective quality metric of the examination device) the examination results are more than a predetermined percentage worse than during an initial phase of the examination, for example, more than 5% or more than 10%. A comparison can also be made with a predetermined quality level instead of with a quality in the initial phase.

Another term or definition for the "examination duration tolerable by the patient" is therefore "examination duration usable by the examination device". This reflects the fact that although in some cases the examination could be continued by the examination device beyond the tolerable examination duration, the examination in the period following the tolerable examination duration cannot be used, for example, because movements by the patient result in the sacrificing of quality above a predetermined threshold.

The phrase "in and/or on the examination device" encompasses both examinations in which a patient is introduced into a device (for example, into an MRI device, for example, a magnetic resonance scanner) and examinations in which a patient is pressed against the examination device (or vice versa), in which the patient is clamped into an examination device. The dwell capability in and/or on the examination device can therefore also be termed or defined as "dwell capability of the patient in an examination conducted by means examination device".

This object is achieved according to the invention by a method wherein an observation phase is initiated in which the patient is observed, and ascertaining at least one measurement parameter relating to the patient during the observation phase. The at least one determined measurement parameter serves as an input into an estimation. The estimation algorithm is executed in an examination duration tolerable by the patient by means of the algorithm, and termination of the observation phase of the patient.

Ascertaining the at least one measurement parameter can in particular include measuring the at least one measurement parameter (i.e. at least one of the measurement parameters).

As used herein, measurement parameter relating to the patient means a measurement parameter that is measured on the patient, i.e. which indicates a current physical property of the patient. It is alternatively or additionally conceivable to ascertain a measurement parameter relating indirectly to the patient such as, for example, a property of the air inside the examination device (for example, in a tunnel of an MRI examination device), while the patient is located therein. Ascertaining a measurement parameter may also include taking a photograph or recording a video and evaluating features in the photograph or video to determine the measurement parameter.

It is clear that the tolerable examination duration determined by the algorithm is an estimate and not a measurement for the patient by the algorithm. The "determined tolerable examination duration" thus can also be referred to as "determined tolerable examination duration to be expected" or the like. Where instead the actual tolerable examination duration, which may differ from the determined expected examination duration, is meant, this is referred to as "actual tolerable examination duration" or the like.

The examination of the patient by means of the examination device can, for example, be initiated during the observation phase. In this case, in addition to the previously ascertained measurement parameters, further measurement parameters can also be advantageously ascertained, for example, by means of the examination device itself.

During the observation phase, the same measurement parameter or measurement parameters can be repeatedly detected several times (i.e. measured values are determined several times for the same measurement parameter or measurement parameters, for example, a continuous measurement of a respiratory rate as a measurement parameter).

Alternatively, at least one first measurement parameter can be determined during a first part of the observation phase prior to the examination and that at least one second measurement parameter is determined during a second part of the observation phase during the examination. The first measurement parameters may be identical to the second measurement parameters, have common measurement parameters, or be completely different.

For example, a respiratory rate of the patient could be measured continuously during the first part, while in the second part in addition, examination results of the examination device (for example, quality metrics of a recorded image) act as additional measurement parameters.

Alternatively, the examination of the patient can be started only after the completion of the observation phase of the patient.

The observation phase can be started outside and separately from the examination device, for example, in a preliminary discussion with the patient or the like.

Preferably, the observation phase takes place partially or entirely while the patient is already arranged in and/or on the examination device, for example, after the patient is introduced into an MRI tunnel. Any sensors integrated in the examination device can also be used advantageously for this purpose.

The at least one measurement parameter determined during the observation phase can be, for example, one or more of:
   A heart rate of the patient;
   A respiratory rate of the patient;
   A respiratory rhythm of the patient;
   A behavioral pattern of the patient (for example, excited speech, humming, singing, etc.);
   A movement pattern of the patient; and/or
   A frequency and/or intensity of physical movements of the patient, in particular of the feet of the patient.

An increased heart rate, an increased respiratory rate, an abnormal respiratory rhythm or an increase in frequency and/or intensity of physical movements, in particular of the feet, may, for example, indicate nervousness of the patient and consequently, a reduced dwell capability and thus a limited tolerable examination duration.

Methods for detecting the nervousness of a person based on the frequency and/or intensity of physical movements are, for example, known from counter-terrorism, wherein automatic evaluations of camera images of a crowd are used to detect which people are displaying a comparatively high level of nervousness. Corresponding algorithms can thus be used in the method according to the invention.

The at least one measurement parameter is advantageously determined unnoticed by the patient during the observation phase, for example, by sensors integrated in a patient table that is arranged in and/or on the examination device, 2D or 3D cameras and/or pilot signal data.

Alternatively or in addition, the determination of the at least one measurement parameter can also be carried out by at least one observation sensor attached to the patient (for example, a motion meter, heart rate meter, respiratory rate meter, and/or the like). It is also possible that a preliminary examination for determining the at least one measurement parameter is carried out on the patient, for example by a further examination device, for example a heart rate measurement, a blood pressure measurement and/or the like.

Accordingly, establishing the availability of the patient for the observation phase (i.e. preparing the observation phase) may take many different forms, for example:
   Guiding the patient into an observation room which is equipped with at least one observation sensor for measuring the at least one measurement parameter;
   Attaching at least one observation sensor to the patient, for example a motion meter, heart rate monitor, respiratory rate meter and/or the like;
   Arranging the patient in and/or on the examination device, for example, introducing the patient into an MRI tunnel.

Advantageously, the adaptation of the examination parameters (in particular, those influencing the examination duration) of the examination device (for example, an image resolution, a number of recordings and the like) takes place on the basis of the determined tolerable examination duration (and/or dwell capability and/or examination duration usable by the examination device) of the patient.

Preferably, the adaptation of the examination parameters of the examination device takes place such that the examination duration is adapted by control of the examination device, such that it is smaller than the determined examination duration tolerable by the patient.

The determination of the at least one measurement parameter can take place once during the observation phase. The determination of the at least one measurement parameter preferably takes place repeatedly during the observation phase, particularly preferably regularly or permanently.

The adaptation of the examination parameters can take place such that the examination by the examination device lasts as long as possible, but no longer than the estimated examination duration that is tolerable by the patient. In other words, the adaptation of the examination parameters advantageously takes place in such a way that the examination is carried out by the examination device with those examination parameters that achieve the best possible examination result, provided that the specific examination duration that can be tolerated by the patient is not exceeded. Criteria for the "best possible examination results" may vary from application to application.

The method for determining the dwell capability can therefore also be a method for operating the respective examination device, in particular if the examination parameters of the examination device are adapted (or set) automatically based on the determined examination duration tolerable by the patient.

In variants of the method according to the invention, the estimation algorithm is an artificial neural network, in particular a deep learning optimized artificial neural network. In other words, the algorithm can be used to process the at least one determined measurement parameter of an artificial neural network, in particular a deep learning-optimized artificial neural network.

The artificial neural network can be trained, for example, on the basis of training data sets which, on the one hand, have vectors with measurement parameters and which, on the other hand, have a respective tolerable examination duration of the patient from which the respective measurement parameters originate as a label or ground truth. These training data sets may originate, for example, from different patients. The algorithm is then possibly less accurately tailored to the particular patient whose dwell capability is to be determined, but can nevertheless operate more accurately overall than if only the (smaller) number of data sets available from the patient were used.

In a further variant of the method according to the invention, the algorithm can be trained in advance in a (predetermined, automatically determined or freely adjustable period of time) prior to processing the at least one determined measurement parameter during a learning phase with a sufficiently large number of data sets associated with that patient in order to provide the algorithm with a sufficient database when used in its application phase (i.e. during processing). This learning phase of the algorithm can advantageously overlap or be the same as the observation phase. The time during the observation phase can thus be used efficiently to simultaneously better train the algorithm.

Alternatively or in addition, the algorithm used can be trained in advance (i.e. in particular, before the observation phase) on the basis of data sets for the generation of which at least one of the measurement parameters determined during the observation phase is determined, and an associated tolerable examination duration of the patient is determined and stored. In the application phase, the acquired knowledge can now be used for the desired determination of the as yet unknown dwell capability.

If previously, for example, the patient always wriggled his or her feet intensely during the observation phase (measurement parameter) in four previous examinations by means of an MRI device, but then was still able to refrain from doing so until the end of the examination (i.e. tolerable examination duration=maximum examination duration), the algorithm can be trained with the four corresponding training data sets. If, during an actual examination, the patient then wriggles his or her feet intensely again in the observation phase, the algorithm can determine that the tolerable examination duration is nonetheless high.

In another embodiment of the method according to the invention, the observation phase of the patient can be continued beyond the beginning of the examination of the patient by means of the examination device. As a result, it is possible, for example, to respond promptly and appropriately to suddenly changing measurement parameters which can affect the dwell capability of the patient and thus the examination duration tolerable by the patient both positively and negatively.

For example, a respiratory rate of the patient during their examination in an MRI device can increase significantly. A correspondingly trained algorithm can take such changes into account and will thereupon possibly determine that the examination duration tolerable by the patient has been reduced.

In another embodiment of the method, during the examination (once, several times, regularly or permanently) it is checked whether the examination can still be completed with the currently set examination parameters of the examination device or not. If this is the case, the examination can be completed. If this is not the case, the examination can be automatically aborted and/or examination parameters of the examination device can be automatically adapted so that the examination is completed with the adapted examination parameters within the remaining examination duration tolerable by the patient.

Accordingly, in a preferred variant of the method according to the invention, the examination duration during an MRI examination can be adjusted based on the determined examination duration tolerable by the patient, for example once, continuously, regularly, or always while fulfilling predetermined criteria (for example, a deterioration in recording quality above a predetermined threshold). The determined examination duration tolerable by the patient can be handed over to an MRI protocol and the number of MRI recordings and their image quality can be adjusted, in particular optimized, according to a recording duration limited to the determined examination duration that can be tolerated by the patient. The actual examination duration (or recording duration) can be adjusted, in particular by adapting the examination parameters of the examination device.

In order to further refine the algorithm and/or to create a wider database with regard to the respective patient, in a further embodiment of the method according to the invention, after completion of the examination or in the event of necessary cancellation due to poor dwell capability of the patient, the actual examination duration can be determined. This can be used for further training of the algorithm, in particular, in connection with the measurement parameters which were ascertained in the observation phase.

It can be required that an operator first confirm the use of such a data set for further training of the algorithm. Alternatively, any such data set can be used automatically for further training of the algorithm.

For more reliable measurement of the at least one measurement parameter, in a further variant of the method according to the invention the at least one measurement parameter can be ascertained by means of sensors of the examination device, for example, by 2D or 3D cameras integrated in the examination device.

Moreover, physiological data (as an example of measurement parameters) can, for example, be determined, in particular, measured, with appropriate sensors, for example, attached to the body of the patient or located in the immediate vicinity of the patient. This takes place advantageously without the patient being restricted thereby. In this case, appropriate sensors are integrated, for example, in a table pertaining or assigned to the examination device. Furthermore, the measurement parameters to be detected can be determined, for example, by means of measuring coils arranged on the skin of the patient. The data to be evaluated accordingly may be available, for example, as pilot signal data which is first demodulated before its evaluation.

Another type of data in which the measurement parameters can be present can be, for example, 2D or 3D camera data, which may depict the observation of the patient before and optionally also during an examination.

In the method according to the invention, one or more of a series of different measurement parameters can in principle be detected which can be used for a subsequent classification of the dwell capability of the respective patient in an appropriate manner. In this case, the measurement parameters may preferably include, but are not limited to, a heart rate, a respiratory rate, a respiratory rhythm, one or more movement patterns and/or behavioral patterns of the patient.

The patient can also continue to be observed using the proposed method during the examination, and the at least one measurement parameter determined in order to establish a possible change (reduction or extension) in the examination duration tolerable by the patient.

If, for example, the heart rate, or for example, movements of the feet of the patient, increase (or decrease) during measurement, this may accordingly indicate a reduction (or extension) of the tolerable examination duration. In addition, further data not specifically mentioned here may be present and used for evaluation.

The aforementioned object is also achieved by a diagnostic examination apparatus that is designed to carry out the method according to the invention.

In particular, the object is achieved by a (diagnostic) examination apparatus, which has an observation device for observing a patient to be examined and a calculation device. The observation device is designed to initiate an observation phase, to ascertain at least one measurement parameter during the observation phase and to terminate the observation phase. The calculation device is designed to process the at least one ascertained measurement parameter using an algorithm in order to determine the examination duration tolerable by the patient to be examined.

The observation device and/or the calculation device can be adjusted according to one of the described advantageous modifications, variants or developments of the method according to the invention and vice versa.

The examination apparatus may also have a control computer which is designed to set and/or adjust the examination parameters of the examination device automatically based on the ascertained examination duration tolerable by the patient to be examined. The adjustment of the examination parameters by the control device can in particular, take place as described in detail above with regard to the method according to the invention.

The present invention also encompasses a non-transitory, computer-readable data storage medium encoded with programming instructions that, when the storage medium is loaded into a computer, cause the computer to implement any or all embodiments of the method according to the invention, as described above.

The data storage medium can be a semiconductor storage medium, for example, an SSD hard drive, a CD, a Blu-ray® disc, a DVD or the like.

The above embodiments and developments can, if appropriate, be combined with one another as desired. Further possible embodiments, developments and implementations of the invention also include combinations of features of the invention which have not been explicitly mentioned above or described below with respect to the exemplary embodiment. In particular, those skilled in the art may also add individual aspects as improvements or supplements to the respective basic form of the present invention.

DESCRIPTION OF THE PREFERRED EMBODIMENTS

Figure 1:
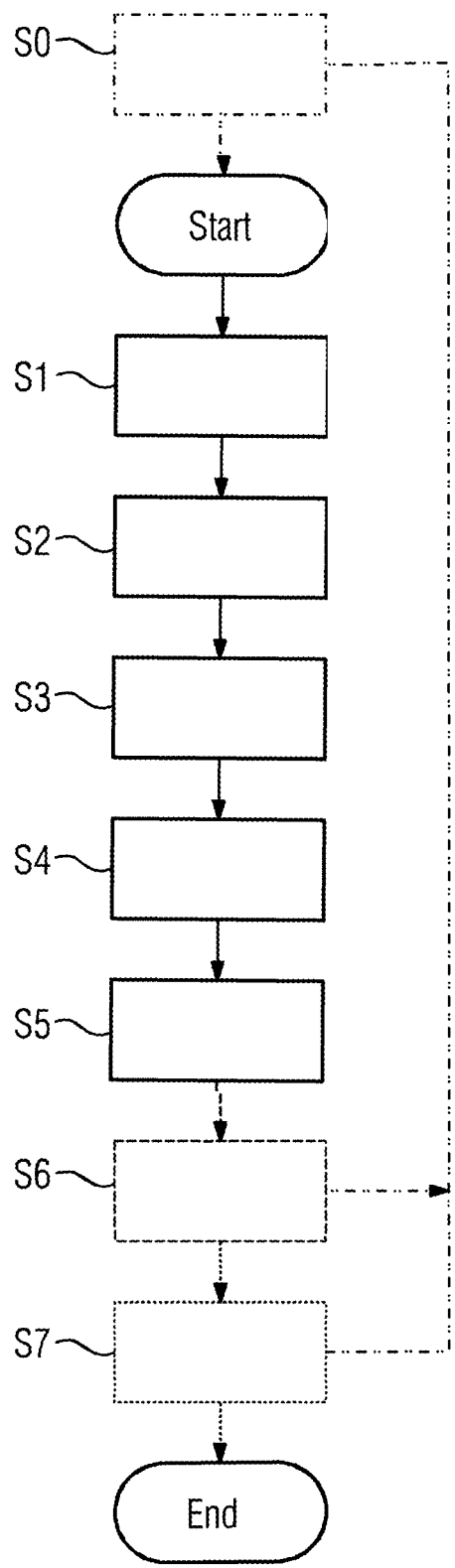
FIG. 1 is a flowchart of an embodiment of the method according to the invention for determining an examination duration tolerable by a patient in and/or on a diagnostic examination device.

In FIG. 1, following a starting point of the method, a first method step S1 is shown, in which a person is supplied as a patient for a diagnostic examination by an MRI examination device, as a result of which the availability of the patient in the preliminary stage of the examination is ensured. More precisely, the patient is introduced into a tunnel of the MRI examination device in the present exemplary embodiment.

At a preset or adjustable time prior to the actual examination of the patient in the MRI examination device, the observation phase, in which the patient is observed, begins in the method step S2 shown. The observation phase started in this method step S2 can be ended both before the start of the examination by means of the MRI examination device, as well as during the examination and extend, for example, to the end of the examination.

In a subsequent method step S3, which is carried out during the observation phase, physiological measurement parameters of the patient are determined by measuring the heart and respiratory rate of the patient and by recording 3D camera data, for example by means of an observation device of the examination device.

In a method step S4, the measurement parameters determined in method step S3 are entered into an algorithm and processed by this algorithm, for example, in a computing device of the examination device.

In a method step S5, the examination duration which can currently be tolerated by the patient to be examined is determined by the algorithm, in particular, using a trained artificial neural network.

The observation phase of the patient is ended in a method step S6, which is shown in a dashed line following the method step S5. The termination of the observation phase can, however, also take place at another, in particular also earlier, juncture of the method, for example, if sufficient relevant data has already been obtained by determining the measurement parameters, or a continuation of the observation according to an abort criterion no longer makes sense and/or the entire examination has to be aborted.

A method step S7, which is illustrated by a dotted line, illustrates an optional adjustment or adaptation of examination parameters of the MRI examination device which influence the examination duration, such as, for example, the number of recordings to be carried out based on the examination duration determined by the algorithm and tolerable by the patient.

This method step S7 is optional because it is also possible that the correct examination duration has already been set, for example, because the number of images for a particular resolution correlates with the ascertained examination duration tolerable in the specific case, i.e. the determined examination duration tolerable by the patient is greater than or equal to the examination duration required for the currently performed examination.

A method step S0 illustrated in dashed-dotted lines in FIG. 1 represents a likewise optional feedback component of the method in which, on completion of the examination, the actual examination duration is determined and (advantageously only after confirmation by an operator) used for further training, as an extension of the learning phase, of the algorithm.

At the same time, the method step S0 illustrated in dashed-dotted lines also represents the circumstance that the algorithm used can be operated by means of at least one optimized artificial neural network which, in particular, is optimized by means of Deep Learning. The artificial neural network can be trained in the method step S0, as described in detail above.

In principle, after determination of the examination duration tolerable by the patient by means of the algorithm, the method according to the invention can also end with the end point according to one of the method steps S5, S6 or S7, without extending the learning phase of the algorithm.

In some variants, the actual diagnostic examination follows. As aforementioned, however, the method can also be continued while the examination is already taking place in order, for example, to enable a continuous adaptation of the possibly spontaneously changing dwell capability VF (and thus the tolerable examination duration) of the patient.

Figure 2:
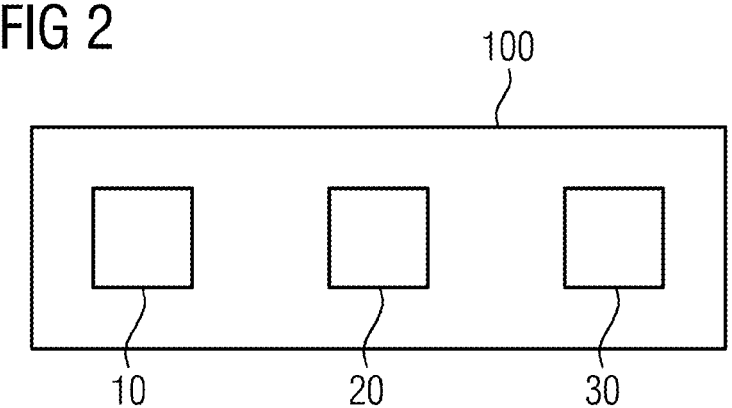
FIG. 2 is a block diagram of a diagnostic examination apparatus according to an embodiment of the present invention.

FIG. 2 shows a diagrammatic block diagram of a diagnostic examination device 100 according to an embodiment of the present invention.

The examination device 100 has an observation device 10 for observing a patient to be examined and a calculation processor 20. The observation device 10 is designed to initiate an observation phase, to ascertain at least one measurement parameter during the observation phase and to terminate the observation phase, preferably according to one of the embodiments and variants described above.

The calculation processor 20 is designed to process the at least one ascertained measurement parameter using an algorithm' in order to determine the examination duration tolerable by the patient to be examined, preferably according to one of the embodiments and variants described above.

The examination device 100 may also have a control computer 30 that is designed to set and/or adjust examination parameters of the examination device 100 automatically based on the ascertained examination duration tolerable by the patient to be examined. The adjustment of the examination parameters by the control computer 30 can in particular take place as described in detail above with reference to the method according to the invention.

The control computer 30 can be designed to set the examination parameters so that an examination is performed with an examination duration which is shorter than or equal to the examination duration tolerable by the patient, as described above.

Figure 3:
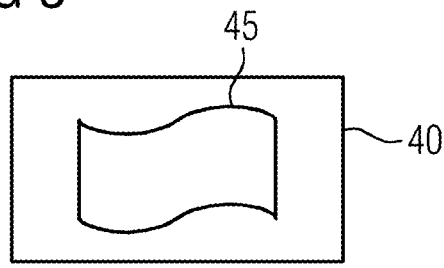
FIG. 3 is a block diagram illustrating a computer program product according to an embodiment of the present invention.

FIG. 3 shows a block diagram as an illustration of a computer program product 40 according to an embodiment of the present invention. The computer program product 40 comprises executable program code 45 which is designed, when executed, to perform the method according to the invention, preferably the method according to one of the embodiments and variants described, for example, the method according to FIG. 1.

Figure 4:
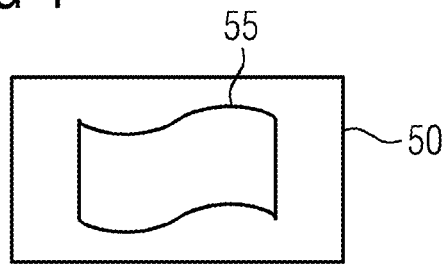
FIG. 4 is a block diagram illustrating a data storage medium according to an embodiment of the present invention.

FIG. 4 shows a diagrammatic block diagram as an illustration of a data storage medium 50 according to an embodiment of the present invention. The data storage medium 50 is a non-volatile computer-readable data storage medium comprising executable program code 55. The executable program code 55 is designed, when executed, to perform the method according to the invention, preferably the method according to one of the embodiments and variants described, for example, the method according to FIG. 1.

The data storage medium 50 can be a semiconductor storage medium, for example, an SSD hard drive, a CD, a Blu-ray® disc, a DVD or the like.

Although the present invention has been described above with reference to preferred exemplary embodiments, it is not restricted thereto, but can be modified in a wide variety of ways. In particular, the invention can be altered or modified in a variety of ways without departing from the scope of the invention.

The basis of the invention can be summarized as follows: a method for determining an examination duration tolerable by a patient in and/or on a diagnostic examination device and an examination device is proposed. A patient to be examined is observed at least in the preliminary stage of the examination concerned, wherein measurement parameters are ascertained. From the measurement parameters, an algorithm determines a statement about the dwell capability of the patient in the examination device. The algorithm used preferably is an artificial neural network.

The invention claimed is:

1. A method for determining an examination duration tolerable by a patient in and/or on a diagnostic examination device, said method comprising:
   initiating an observation phase in which the patient is observed;
   ascertaining a measurement parameter relating to the patient during the observation phase;
   in a computer, using the determined measurement parameter as an input to an estimation algorithm;
   executing, via the computer, the estimation algorithm to generate an expected examination duration of the patient as an output of the estimation algorithm;
   terminating the observation phase of the patient at a time after the output is generated; and
   setting or adjusting examination parameters of the diagnostic examination device in response to the generated expected examination duration such that a duration of an examination of the patient via the diagnostic examination device does not exceed the expected examination duration the patient.

2. The method as claimed in claim 1, wherein the estimation algorithm is executed as part of an artificial neural network.

3. The method as claimed in claim 1, further comprising:
   training the estimation algorithm during a learning phase with a number of data sets associated with the patient before executing the estimation algorithm to produce the expected examination duration.

4. The method as claimed in claim 3, comprising wherein the act of training the estimation algorithm comprises training the estimation algorithm using data sets that associate the measurement parameter of the patient with a respective examination duration that is tolerable by the patient.

5. The method as claimed in claim 1, further comprising:
continuing the observation phase of the patient beyond a beginning of the examination of the patient in and/or on the examination device.

6. The method as claimed in claim 5, further comprising: adjusting an examination duration performed via the examination device at least once during the examination of the patient.

7. The method as claimed in claim 1, further comprising:
training the estimation algorithm, during a learning phase, with a number of data sets associated with the patient (i) before executing the estimation algorithm to generate the expected examination duration, and (ii) after completion or discontinuation of the examination of the patient in and/or on said diagnostic examination device,
wherein the examination duration of the examination of the patient is used as a further one of the data sets for the training of the estimation algorithm.

8. The method as claimed in claim 1, further comprising:
ascertaining the measurement parameter using a sensor of the examination device.

9. The method as claimed in claim 1, further comprising:
ascertaining the measurement parameter using a sensor attached to the patient.

10. The method as claimed in claim 1, further comprising:
ascertaining the measurement parameter from the group consisting of a heart rate of the patient, a respiratory rate of the patient, a respiratory rhythm of the patient, a movement pattern of the patient, and a behavioral pattern of the patient.

11. A diagnostic examination apparatus, comprising:
a diagnostic examination device with which a patient interacts to conduct an examination of the patient in and/or on said diagnostic examination device;
an observational device configured to initiate an observation phase in which the patient is observed;
a computer configured to control ascertaining a measurement parameter relating to the patient during the observation phase,
wherein the computer is configured;
use the determined measurement parameter as an input to an estimation algorithm,
execute the estimation algorithm to generate an expected examination duration of the patient as an output of the estimation algorithm;
terminate the observation phase of the patient at a time after the output is generate; and
setting or adjusting examination parameters of the diagnostic examination device in response to the generated expected examination duration such that a duration an examination of the patient via the diagnostic examination device does not exceed the expected examination duration ref the patient.

12. A non-transitory, computer-readable data storage medium encoded with programming instructions, the storage medium being configured to be loaded into a computer associated with a diagnostic examination device with which a patient interacts to conduct an examination of the patient with the diagnostic examination device, the programming instructions causing the computer to:
initiate an observation phase in which the patient is observed;
ascertain a measurement parameter relating to the patient during the observation phase;
use the determined measurement parameter as an input to an estimation algorithm;
execute the estimation algorithm to generate an expected examination duration of the patient as an output of the estimation algorithm;
terminate the observation phase of the patient at a time after the output is generated; and
setting or adjusting examination parameters of the diagnostic examination device in response to the generated expected examination duration such that a duration of an examination of the patient via the diagnostic examination device does not exceed the expected examination duration of the patient.

13. The method as claimed in claim 1, wherein the determined measurement parameter comprises a quality metric of a recorded image of the patient acquired by the diagnostic examination device during the observation phase.

14. The method as claimed in claim 1, wherein the expected examination duration of the patient comprises a computed time period during which the patient is examined via the diagnostic examination device in accordance with a respective quality metric that exceeds a predetermined quality metric threshold.

15. The method as claimed in claim 1, wherein the determined measurement parameter comprises a measurement of patient motion during the observation phase.

16. The method as claimed in claim 1, wherein the parameters of examination comprise a number of recordings to be carried out via the diagnostic examination device.

* * * * *